US00PP36285P2

(12) United States Plant Patent
Layt

(10) Patent No.: US PP36,285 P2
(45) Date of Patent: Dec. 3, 2024

(54) ***WESTRINGIA* PLANT NAMED 'WES10'**

(50) Latin Name: *Westringia fruticosa*
Varietal Denomination: WES10

(71) Applicant: Todd Anthony Layt, Richmond (AU)

(72) Inventor: Todd Anthony Layt, Richmond (AU)

( * ) Notice: Subject to any disclaimer, the term of this patent is extended or adjusted under 35 U.S.C. 154(b) by 0 days.

(21) Appl. No.: 18/445,967

(22) Filed: Apr. 19, 2024

(51) Int. Cl.
*A01H 5/02* (2018.01)
*A01H 6/70* (2018.01)

(52) U.S. Cl.
USPC ..... Plt./226

(58) Field of Classification Search
USPC ..... Plt./226
See application file for complete search history.

*Primary Examiner* — Karen M Redden
(74) *Attorney, Agent, or Firm* — Samuel R. McCoy, Jr.

(57) ABSTRACT

'WES10' is a distinctive variety of *Westringia* plant which is characterized by the combination of a compact and globose growth habit, broadly ovate foliage with an obtuse apex, variegated foliage, an abundance of small white flowers in spring, and the stability of all characteristics from generation to generation.

2 Drawing Sheets

Latin name of the genus and species: The Latin name of the genus and species of the novel variety disclosed herein is *Westringia fruticosa.*

Variety denomination: The inventive variety of *Westringia fruticosa* disclosed herein has been given the variety denomination 'WES10'.

BACKGROUND OF THE INVENTION

Parentage: 'WES10' is a spontaneous partial-plant mutation which was discovered in 2022 growing amongst a cultivated population of *Westringia fruticosa* 'WES04' (U.S. Plant Pat. No. 25,675), at a commercial plant breeding facility in Clarendon, New South Wales, Australia. The mutation was first noted for its unique variegated leaves relative to those of the parent plant and was subsequently isolated for further evaluation in order to confirm the distinctness and stability of the characteristics first observed. Upon confirmation of distinctness and stability, the new *Westringia* plant was selected for commercialization and given the name 'WES10'.

Asexual Reproduction: 'WES10' was first propagated asexually by semi-hardwood cuttings in Clarendon, New South Wales, Australia in 2022 and has since been asexually propagated by vegetative cuttings through three successive generations. The distinctive characteristics of the inventive 'WES10' variety are stable from generation to generation; clones of the variety produced by asexual reproduction maintain the distinguishing characteristics of the original plant.

SUMMARY OF THE INVENTION

The cultivar 'WES10' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Westringia* cultivar, 'WES10'.

1. *Westringia* 'WES10' exhibits a compact, densely-foliage, globose growth habit with a relatively short plant height; and
2. *Westringia* 'WES10' exhibits broadly elliptical foliage with an obtuse apex, tightly arranged in whorls along the greyed-green, glaucous stems; and
3. *Westringia* 'WES10' exhibits glaucous juvenile foliage that is dark greyed-green and broadly margined with yellow on the adaxial surface, and very light greyed-green, narrowly margined with yellow, on the abaxial surface; and
4. *Westringia* 'WES10' exhibits glaucous mature foliage that is dark greyed-green and broadly margined white with light yellow suffusion on the adaxial surface, and an abaxial surface that is very light greyed-green and narrowly margined white with light yellow suffusion; and
5. *Westringia* 'WES10' exhibits an abundance of small, white, solitary flowers in spring and sporadically during the summer.

BOTANICAL DESCRIPTION OF THE PLANT

Figure 1:
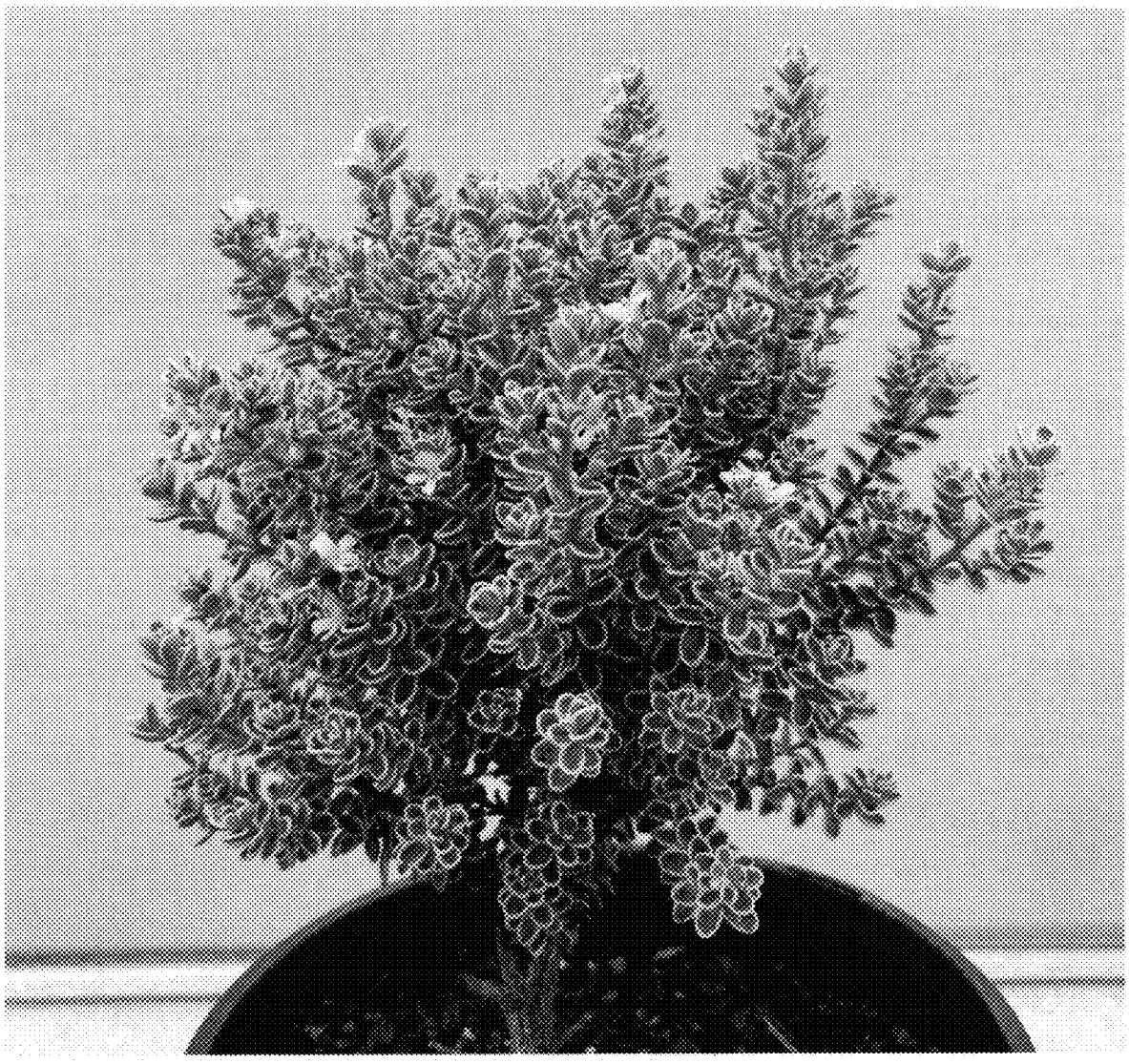
FIG. 1 shows, as nearly true as it is reasonably possible to make the same in color illustrations of this type, an exemplary 'WES10' plant. The plant shown is approximately 12 months old, planted in a 200 mm nursery container, in Clarendon, New South Wales, Australia.
Figure 2:
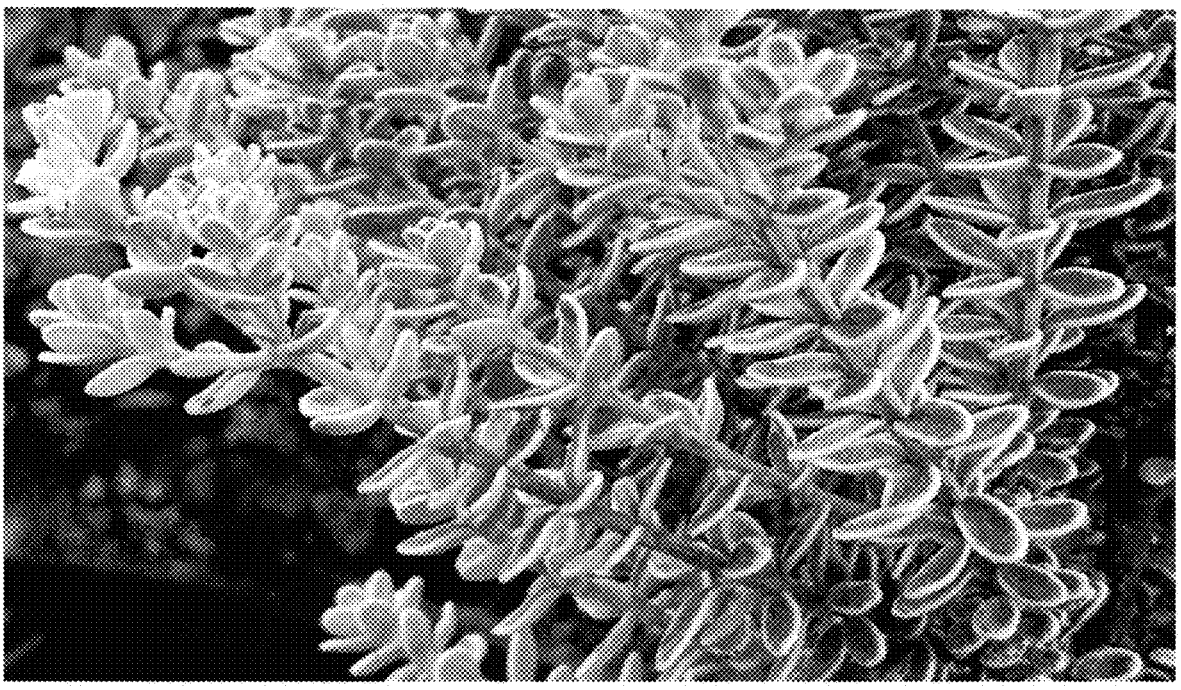
FIG. 2 shows, as nearly true as it is reasonably possible to make the same in color illustrations of this type, the typical juvenile and mature foliage of 'WES10'.

The following is a detailed botanical description of a new and distinct variety of a *Westringia fruticosa* plant known as 'WES10'. Unless indicated otherwise, the descriptions disclosed herein are based upon observations made in March of 2024 from a 12-month-old 'WES10' plant, grown outdoors in a 200 mm nursery container, in Clarendon, New South Wales, Australia. The observed plant was maintained with granular slow-release fertilizer and regularly watered with overhead irrigation. No pest and disease measures were taken.

Those skilled in the art will appreciate that certain characteristics will vary with older or, conversely, younger plants. 'WES10' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart,* The Royal Horticultural Society, London, 1986 edition.

General plant description:

*Plant habit.*—Compact, globose, densely-foliaged growth habit.

*Vigor.*—Vigorous.

*Growth rate.*—Fast-growing.

*Height.*—42 cm.

*Width.*—39 cm.

*Bloom period.*—Spring and sporadically at other times of year, depending on climate.

*Hardiness.*—USDA Zone 9 to 11.

*Propagation.*—Method — Propagation is accomplished using semi-hard wood cuttings. Roots well without rooting compound or hormone. Time to develop roots — Approximately 21 days at 20 degrees Celsius. Crop time — From approximately six to eight months are needed to produce a well rooted 14 cm nursery pot, starting from a rooted cutting. Crop time varies with location and production practices.

*Pest and disease susceptibility or resistance.*—Not any more or less susceptible to pests or diseases known to affect *Westringia fruticosa.*

*Cultural tolerances.*—*Westringia* is commonly known to perform well in sandy soils, but also tolerates heavy, clay-type soils well. 'WES10' can also be grown in a relatively wide pH range and is also tolerant of above-normal salt concentration in the soil environment and is also tolerant of aerosol salt exposure. 'WES10' has good drought tolerance, once established.

Roots: The roots of 'WES10' are colored white, nearest to RHS 155C, fleshy and thick, similar to other *Westringia* species and cultivars.

Stem:

*General habit.*—Multiple main stems; basally branched; freely branching habit.

*Attitude.*—Upright.

*Aspect.*—Terete, yet angular.

*Stem dimensions.*—The longest of any mature stems is approximately 35 to 38 cm in length with a diameter of 8 to 9 mm near the base.

*Internode length.*—1.2 cm on average.

*Stem strength.*—Moderately strong.

*Texture.*—Juvenile stems are lightly pubescent; mature stems are glabrous and corky; both juvenile and mature stems are glaucous.

*Color, juvenile and mature stems.*—Nearest to a mixture of green, RHS 138B, and greyed-green, RHS 194B.

*Color, oldest wood.*—Brown, nearest to in between RHS 200A and 200B, with grey-brown, RHS199D, striations at maturity.

Foliage:

*Shape.*—Broadly elliptical.

*Division.*—Simple.

*Apex.*—Obtuse.

*Base.*—Cuneate.

*Margins.*—Entire.

*Arrangement.*—Whorled.

*Attachment.*—Petiolate.

*Texture, adaxial and abaxial surfaces.*—Glabrous; coriaceous; heavily glaucous.

*Texture, adaxial and abaxial surfaces.*—Lightly to moderately pubescent; heavily glaucous.

*Luster, adaxial and abaxial surfaces.*—Matte.

*Mature leaf dimensions.*—1.4 cm long and 0.6 cm wide.

*Color.*—Juvenile color, adaxial surface — Greyed-green, nearest to RHS 189A and mottled with 191A; broadly margined with yellow, nearest to RHS 4B. Juvenile color, abaxial surface — Greyed-green, nearest to RHS 192A; narrowly margined with yellow, nearest to RHS 4B. Mature color, adaxial surface — Greyed-green, nearest to RHS 189A and mottled with 191A; broadly margined with white, nearest to RHS 155D, which is lightly suffused with yellow, nearest to RHS 4D. Mature color, abaxial surface — Greyed-green, nearest to RHS 192A; narrowly margined with white, RHS 155D, which is lightly suffused with yellow, nearest to RHS 4D.

*Venation.*—Pattern — Reticulate but very inconspicuous. Color, adaxial surfaces — Indistinguishable from surrounding foliage. Color, abaxial surfaces — Indistinguishable from surrounding foliage.

*Petiole.*—Aspect — Flattened terete. Dimensions — Approximately 2.0 mm in length; diameter is approximately 1.0 mm. Strength — Moderately strong. Texture, adaxial and abaxial surfaces — Lightly to moderately pubescent. Luster, adaxial and abaxial surfaces — Matte. Color, adaxial surface — Greyed-green, RHS 193A. Color, abaxial surface — Greyed-green, RHS 193B.

Inflorescence: Flowers are solitary; no inflorescence.

Flower bud:

*Shape.*—Broad oblong to obovoid.

*Length.*—6.0 mm.

*Diameter.*—3.0 mm.

*Texture.*—Smooth and glabrous.

*Luster.*—Matte.

*Color.*—Greyed-green, nearest to RHS 194A, and suffused lighter, nearest to RHS 194D; emerging flower petals are green-white, nearest to RHS 155C.

Flower:

*Natural flowering season.*—The heaviest flowering occurs in spring, with sporadic flowering through summer.

*Abundance of flowers.*—Abundant.

*Shape, type.*—Bilabiate; sympetalous; irregular.

*Attachment.*—Sessile.

*Aspect.*—Upright to outward.

*Flower longevity on plant.*—Approximately five days.

*Persistent or self-cleaning.*—Self-cleaning.

*Fragrance.*—Non-fragrant.

*Diameter.*—1.2 cm.

*Depth.*—1.3 cm, including the calyx.

*Pedicels*.—None; flowers are sessile.

*Calyx*.—Shape — Campanulate with sepals fused into a bell shape, with free sepal lobes. Length — 0.75 cm. Diameter — 0.5 cm. Sepals — Quantity — 5 fused sepals, with free sepal lobes. Shape of the lobes — Deltoid. Lobe dimensions — 0.3 cm long and 0.325 cm wide. Apex — Acute. Base — Fused. Sepal reflex — Not reflexed. Margin — Entire. Texture, upper surface — Smooth and glabrous; glaucous. Texture, lower surface — Smooth and glabrous; glaucous. Luster, upper surface — Matte. Luster, lower surface — Matte. Color — Inner surface — Yellow-green, nearest to in between RHS 144A and 146B. Outer surface — Yellow-green, nearest to in between RHS 144A and 146B.

*Petals*.—Quantity — 5 petals; two upper petals fused into a large lobe and three lower petals with free lobes. Shape — The petal lobes are spatulate. Apex — Broad emarginate. Base — Fused, forming a floral tube. Margin — Entire; ciliate; moderate undulation. Texture, upper surface — Tomentose. Texture, lower surface — Tomentose. Petal and floral tube color — When opening, inner surface — White, nearest to RHS 155C. When opening, outer surface — White, nearest to RHS 155C. Fully opened, inner surface — The floral tube and petal lobes are white, nearest to RHS 155C, with small orange-red spots at the throat of the floral tube, nearest to RHS 31B; floral tube is suffused with yellow-green, RHS 144B. Flower color does not fade with age. Fully opened, outer surface — The floral tube and petal lobes are white, nearest to RHS 155C. Flower color does not fade with age. Petal venation color — Fully opened, upper surface — White, nearest to RHS 155D. Fully opened, lower surface — White, nearest to RHS 155D.

Reproductive organs:

*Androecium*.—Stamens — Quantity — Approximately 4. Anthers — Attachment — Dorsifixed. Shape — Oblong with longitudinal dehiscence. Dimensions — 0.15 cm long and 0.075 to 0.1 cm wide. Color — White, nearest to RHS 155B. Filaments — Dimensions — 0.35 cm long and approximately 0.075 cm in diameter. Color — White, nearest to RHS 155B. Amount of Pollen — Sparse. Pollen color — Yellow-orange, RHS 15D.

*Gynoecium*.—Pistil — Quantity — 1. Length — 0.55 cm. Style — Dimensions — 0.45 cm long and approximately 0.1 cm in diameter. Color — White, nearest to RHS 155B. Stigma — Shape — Globose. Length — 0.1 cm. Diameter — 0.125 cm. Color — White, nearest to RHS 155B.

Fruit and seed: Not observed.

Comparison With the Parent

Plants of the new cultivar 'WES10' differ from its parent, *Westringia fruticosa* 'WES04' (U.S. Plant Pat. No. 25,675), by the characteristics described in Table 1.

TABLE 1

| Characteristic | 'WES10' | 'WES04' |
|---|---|---|
| Presence of variegation. | Present. | Absent. |
| General coloration of the mature adaxial foliar surface. | Dark greyed-green and margined white with light yellow suffusion. | The entire lamina, including the margins, are a lighter shade of greyed-green relative to 'WES10'. |
| Foliage shape. | Broadly elliptical. | Narrowly elliptical. |
| Foliage apices. | Obtuse. | Acute. |

Comparison With the Most Similar Varieties Known to the Inventor

Plants of the new cultivar 'WES10' may be distinguished from the most similar known commercial comparators, *Westringia fruticosa* 'Smokey' (not patented) and *Westringia fruticosa* 'Morning Light' (not patented), by the characteristics described in Tables 2 and 3, respectively.

TABLE 2

| Characteristic | 'WES10' | 'Smokey' |
|---|---|---|
| Growth habit. | More compact than 'Smokey', with shorter internodes. | Less compact and more freely branching. |
| Plant size. | Smaller than 'Smokey'. | Larger than 'WES10'. |
| General coloration of the mature foliage. | Dark greyed-green and margined white with light yellow suffusion. | Lighter shade of greyed-green, relative to 'WES10', and margined white with light yellow suffusion. |
| Foliage shape. | Broadly elliptical. | Narrowly elliptical. |
| Foliage apices. | Obtuse. | Acute. |
| General coloration of the flowers. | White. | White, lightly suffused with violet. |

TABLE 3

| Characteristic | 'WES10' | 'Morning Light' |
|---|---|---|
| Growth habit. | More compact than 'Morning Light', with shorter internodes. | Less compact and more freely branching. |
| Plant size. | Smaller than 'Morning Light'. | Larger than 'WES10'. |
| General coloration of the mature foliage. | Dark greyed-green and margined white with light yellow suffusion. | Dark greyed-green and margined with cream yellow. |
| Foliage shape. | Broadly elliptical. | Narrowly elliptical. |
| Foliage apices. | Obtuse. | Acute. |

That which is claimed is:

1. A new and distinct variety of *Westringia fruticosa* plant named 'WES10', substantially as described and illustrated herein.

* * * * *